United States Patent
Gamble et al.

(10) Patent No.: US 7,798,021 B2
(45) Date of Patent: Sep. 21, 2010

(54) METHOD AND APPARATUS FOR SAMPLE PROCESSING AND INJECTION

(76) Inventors: Kimberly R. Gamble, 5690 The 12th Fairway, Suwanee, GA (US) 30021; Robert W. Fitzgerald, 4641 Grayling Dr., Apex, NC (US) 27539-8875

( * ) Notice: Subject to any disclaimer, the term of this patent is extended or adjusted under 35 U.S.C. 154(b) by 658 days.

(21) Appl. No.: 11/640,502

(22) Filed: Dec. 18, 2006

(65) Prior Publication Data
US 2007/0157709 A1 Jul. 12, 2007

Related U.S. Application Data

(60) Provisional application No. 60/758,493, filed on Jan. 12, 2006.

(51) Int. Cl.
*G01N 1/20* (2006.01)

(52) U.S. Cl. ................... 73/863.71; 73/864.14

(58) Field of Classification Search ............... 73/863.71
See application file for complete search history.

(56) References Cited

U.S. PATENT DOCUMENTS

| | | |
|---|---|---|
| 3,327,520 A | 6/1967 | Stapp, Jr. |
| 3,635,093 A | 1/1972 | Downs et al. |
| 3,918,913 A | 11/1975 | Stevenson et al. |
| 3,991,627 A | 11/1976 | Laird et al. |
| 4,435,176 A * | 3/1984 | Ishikawa ................. 604/190 |
| 4,585,435 A | 4/1986 | Vaillancourt |
| 4,713,974 A | 12/1987 | Stone |
| 4,787,971 A | 11/1988 | Donald |
| 4,808,381 A | 2/1989 | McGregor et al. |
| 4,935,010 A | 6/1990 | Cox et al. |
| 4,956,298 A | 9/1990 | Diekmann |
| 4,982,740 A | 1/1991 | Broden |
| 4,995,967 A | 2/1991 | Van Driessche |
| 5,081,872 A | 1/1992 | Greter |
| 5,169,602 A | 12/1992 | Pang et al. |
| 5,251,474 A | 10/1993 | Wardlaw et al. |
| 5,393,674 A | 2/1995 | Levine et al. |
| 5,407,269 A | 4/1995 | Sherry et al. |

(Continued)

FOREIGN PATENT DOCUMENTS

WO WO 2005/042166 A1 12/2005

OTHER PUBLICATIONS

European Search Report, Application No. EP 06 02 7114, dated Aug. 27, 2008, Munich.

*Primary Examiner*—Hezron Williams
*Assistant Examiner*—Mark Shabman
(74) *Attorney, Agent, or Firm*—Shlesinger, Arkwright & Garvey LLP

(57) ABSTRACT

A sample processing/injection device for liquid chromatography comprises a septum at one end of the device, a processing chamber and injection needle disposed on a second end of the device. A fluid sample is transferred into the device by a transfer needle penetrating the septum of the device. The sample device may be positioned to a receiving component such as an injection valve of an instrument by movement of the transfer needle. The sample is injected into the receiving component through the injection needle of the sample processing/injection device through motive pressure supplied by the transfer needle. The sample processing/injection device reduces sampling steps and improves automation by performing sample processing and injection with a single device.

11 Claims, 8 Drawing Sheets

U.S. PATENT DOCUMENTS

| | | |
|---|---|---|
| 5,419,835 A | 5/1995 | Adams et al. |
| 5,567,309 A | 10/1996 | Classon et al. |
| 5,660,796 A | 8/1997 | Sheehy |
| 5,707,589 A | 1/1998 | Fullemann |
| 5,882,601 A | 3/1999 | Kath et al. |
| 5,945,070 A | 8/1999 | Kath et al. |
| 6,083,761 A | 7/2000 | Kedar et al. |
| 6,146,362 A | 11/2000 | Turnbull et al. |
| 6,251,343 B1 | 6/2001 | Dubrow et al. |
| 6,309,608 B1 | 10/2001 | Zhou et al. |
| 6,406,671 B1 | 6/2002 | DiCesare et al. |
| 6,479,298 B1 | 11/2002 | Miller et al. |
| 6,526,812 B2 | 3/2003 | Martin et al. |
| 6,959,615 B2 | 11/2005 | Gamble |
| 7,001,774 B1 | 2/2006 | Gamble et al. |
| 2002/0168778 A1 | 11/2002 | Andrien, Jr. et al. |
| 2004/0069076 A1* | 4/2004 | Gamble .................. 73/863.85 |

* cited by examiner

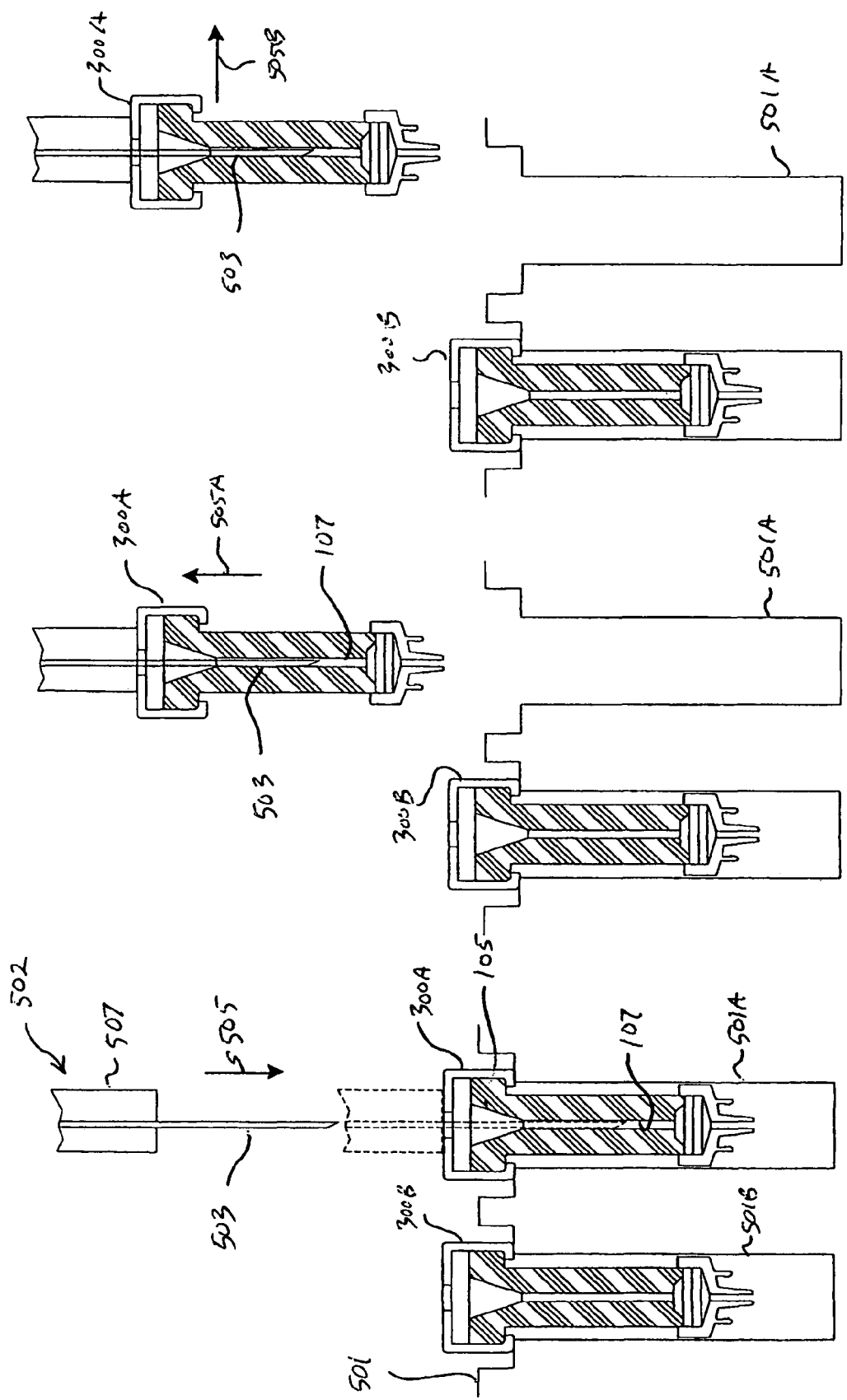

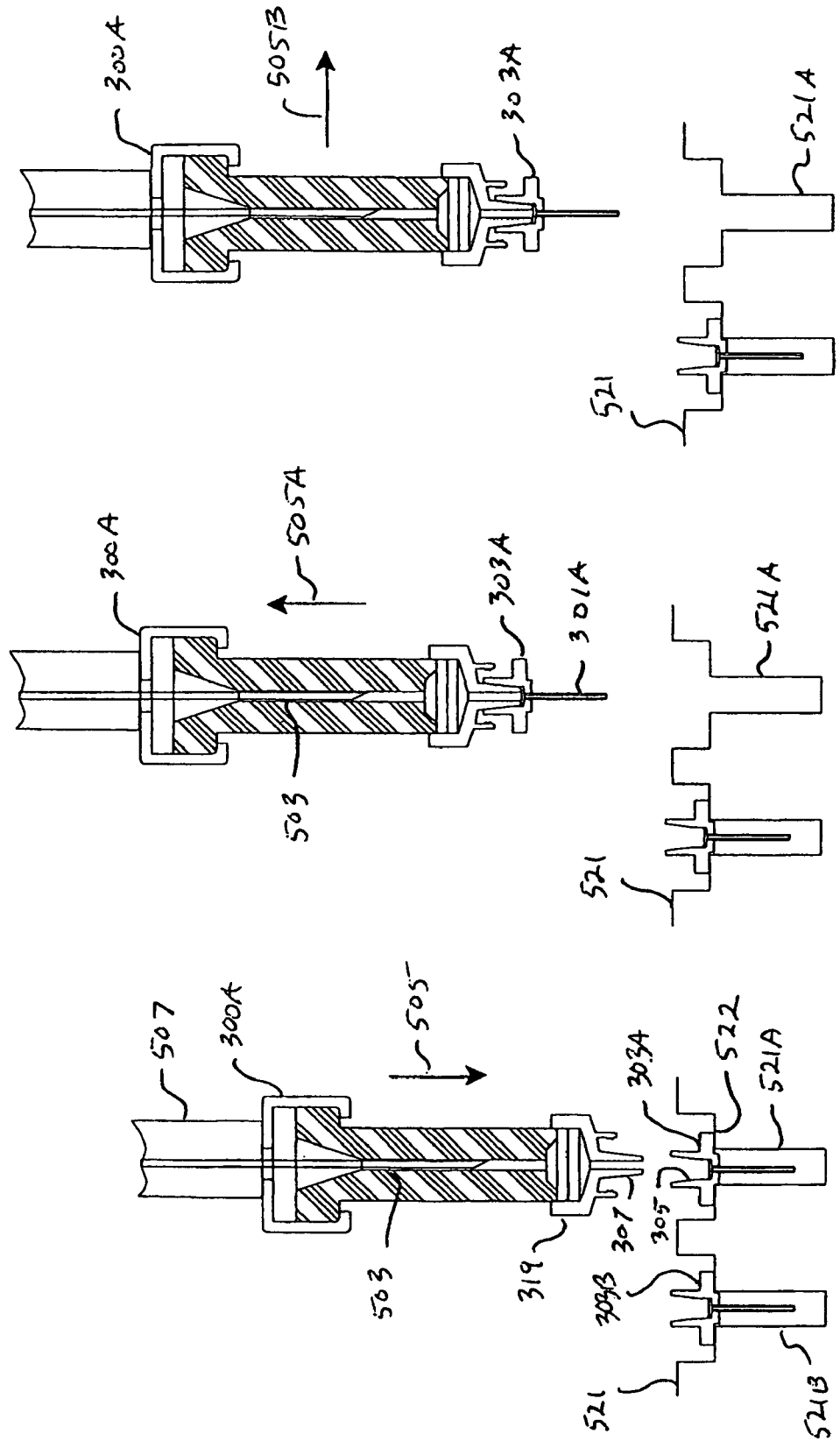

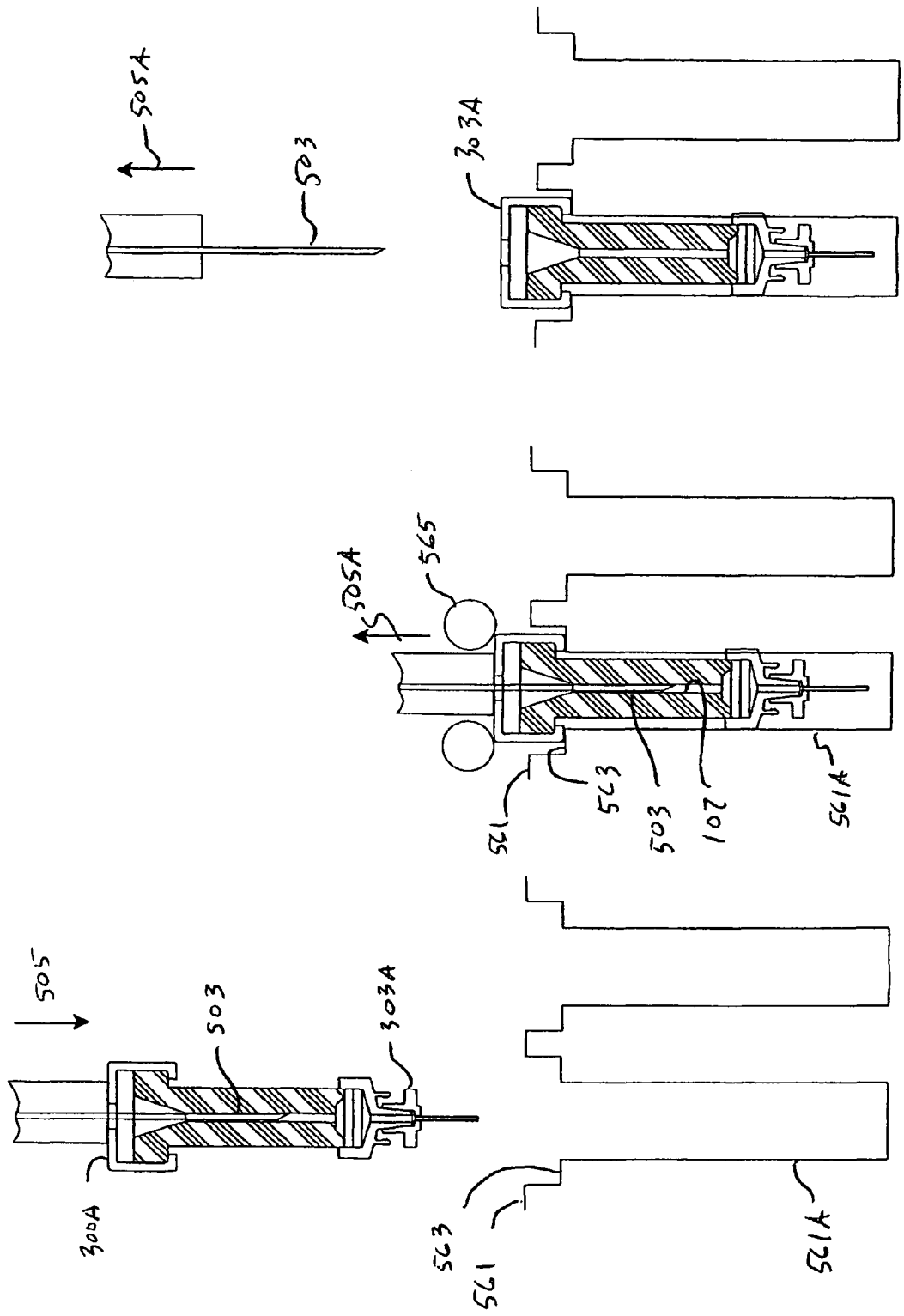

METHOD AND APPARATUS FOR SAMPLE PROCESSING AND INJECTION

RELATED APPLICATION

This is a nonprovisional of provisional application Ser. No. 60/758,493, filed Jan. 12, 2006, incorporated herein by reference.

FIELD OF THE INVENTION

The present invention relates to sample processing and, more particularly, to a method and apparatus for automated sample handing, processing and testing utilizing a sample processing/injection device.

BACKGROUND OF THE INVENTION

The growth in medical and pharmaceutical research as well as diagnostic analysis and testing has created a need for equipment and procedures for low cost, high-speed sample collection and processing. Automated equipment is available for filling and retrieval of samples from sample wells, vials, bottles and other containers.

Microplates comprising a plurality of sample wells provide a convenient means to handle and store samples. Automated equipment positions microplates for sample filling, retrieving, and analysis. Despite improvements in sample handling equipment, many applications require manual labor when performing evolutions such as; preparing sample containers or vials, relocating sample containers, and passing sample fluids through process elements such as absorbents, adsorbents, filters, solid phase extraction mediums, or additive compound materials. Manual processing steps are usually required when sample numbers are insufficient to justify design and building custom automated equipment.

Often the wells of microplates are used as the sample containers. In other applications, vials or sample bottles are inserted into the wells of microplates to contain the samples or testing fluids.

Certain types of testing such as chromatography, combinatorial chemistry, or high-throughput screening utilize processing of a sample by a processing element such as solid phase extraction medium, a filter, or an adsorbent disk. The compounds of interest are recovered by passing solvents through the processing element. This process requires multiple steps that are difficult to automate, especially if the sample numbers are not sufficiently large to justify specialized equipment, containers and processes.

Sample processing devices such as those disclosed in U.S. Pat. No. 6,959,615, hereby incorporated as reference, provide a means to withdraw, discharge, process and elute samples from sample vessels including wells of microplates. While this is a significant improvement in reducing the number of steps and devices required for sample collection, processing and testing, intermediate sample vessels are still required between sample collection and sample injection into the final test instrument. Additionally, sample-to-sample exposure is a significant threat to sample integrity and quality of the resulting analytical data.

There exists a need for improved sample collection, processing and testing devices to further reduce processing steps, improve speed and productivity of sample testing evolutions, and perform serial processing on existing automated devices to improve data quality.

OBJECTS AND SUMMARY OF THE INVENTION

Therefore, an object of the present invention is to provide a sample processing/injection device that can be used to collect, process and inject fluid samples.

Another object of the present invention is to provide a sample processing/injection device that can be repositioned by movement of a transfer needle penetrating a septum of the device.

Another object of the present invention is to provide a sample processing/injection device having an injection needle sealable with an injection port of sampling instrument injection valve.

Another object of the present invention is to provide a sample processing/injection device with an injection needle attachable by quick removable connectors such as luer slip and luer lock fittings.

Another object of the present invention is to provide a sample processing/injection device that can be placed in standard multi-well trays.

Still another object of the present invention is to provide a sample processing/injection device that is simple and low in cost.

The sample processing/injection device of the present invention is an elongated tubular structure having a sealing septum on one end and an injection needle on the opposite end. The septum seals a conical needle guide and a reduced diameter through chamber having a close or tight fit with a transfer needle of a manual or automated sampling apparatus. The reduced diameter through chamber opens to a larger diameter processing chamber containing one or more processing elements such as frits, filters or solid phase extraction elements. The processing chamber is in fluid connection with the injection needle. In the preferred embodiments, an in-line fluid communication channel exists between the sealed septum end, reduced diameter through chamber, processing chamber, and injection needle.

In another embodiment, the sample device has a sealing septum on one end and a connector on the opposite end. The connector allows mechanical attachment and fluid communication of the device with an injection needle. In the preferred embodiments, the connector is a quick-connect tapered connector such as a luer slip or a luer-lock connector. The taper portion of the connector may act as a drip tube for sample intake or discharge from the sample processing/injection device.

The close or tight fit of the through chamber with a transfer needle and a through chamber length of at least 5 times the diameter of the through chamber provides both engagement of the transfer needle and sample device and automatic alignment of the device with the transfer needle. The good alignment provided by the fit allows precision movement and placement of the device utilizing only the transfer needle, simplifying instrument design and construction and speeding automated sampling. For example, the device may be transferred to the injection port of a testing machine and the injection needle sealed with the injection port by positioning of the transfer needle alone.

The combination of a luer slip or luer lock connector allows use of a small diameter injection needle compatible with low volume testing injection ports and a larger diameter drip tube portion for fast sample transfer with the injection needle removed. The design also allows use of the connector as a drip tube for fast elution, intake or discharge of sample or wash fluids into our out of the sample device.

The sample processing/injection device with both a drip tube and an injection needle connectable with a quick-connect/disconnect connector allows a number of sampling operations especially suitable for automation. These operations and procedures include: intake or discharging sample or wash fluids quickly into or out of the sample device using the drip tube integral with the connector, or withdrawing or injecting a sample or wash fluid via an injection needle attached by the connector; moving and precise positioning the device with or without an injection needle by movement of a transfer needle inserted into the septum and reduced-diameter through chamber of the sample device; attaching or removing the injection needle to/from the device by movement of the transfer needle inserted into the septum and reduced-diameter through chamber of the sample device and injection of sample fluid into a sample valve by an injection needle attached to the sample device, the positioning and injection needle penetration accomplished by movement of the transfer needle inserted into the septum and reduced-diameter through chamber of the sample device.

These and many other operations are made possible by transfer needle engagement and alignment features of the device and the combination drip tube and injection needle connector of the present invention.

BRIEF DESCRIPTION OF THE DRAWINGS

These and other features, aspects and advantages of the present invention will become better understood with regard to the following description, appended claims and accompanying drawings where:

FIGS. 5A-5L are schematic drawings of process steps showing use of the sample processing/injection device through engagement of a transfer needle with the device to engage the injection needle of the device, to move the device, to transfer sample to a receiving component and to remove the device from the transfer needle portion.

DESCRIPTION OF THE PREFERRED EMBODIMENTS

Figure 1:
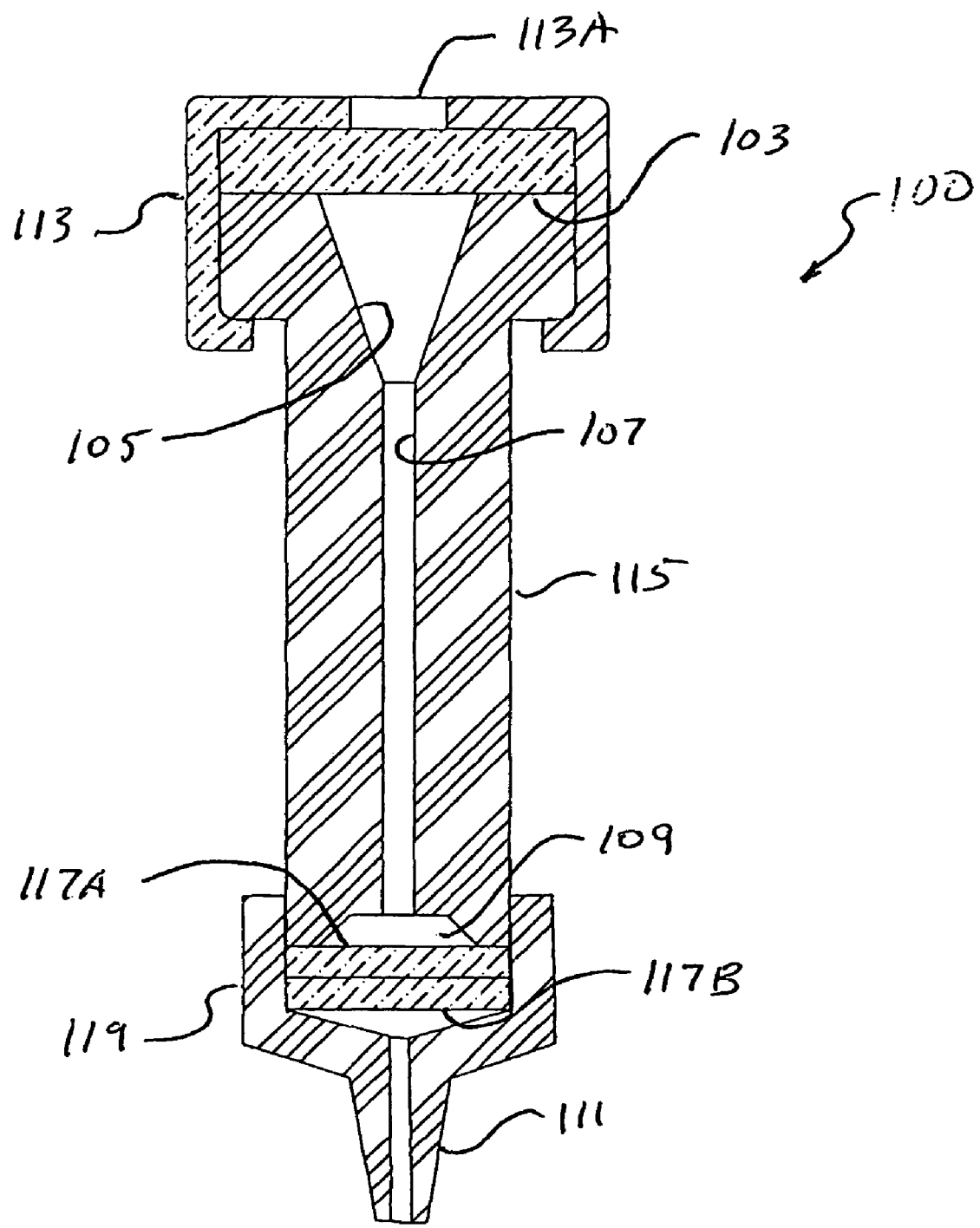
FIG. 1 is cross section elevation drawing of a prior art sample processing device.

FIG. 1 is a cross section drawing of a prior art sample processing device 100 for retrieving, processing and discharging samples. The device utilizes a penetrable septum 103, a conical needle guide 105, a reduced diameter through chamber 107, a processing chamber 109 and a drip tube 111. A top cap, such as a crimp cap 113 secures septum 103 to a body portion 115 of the device. Cap aperture 113A provides access of a needle (not shown) into the device. Sample processing elements such as filters or frits 117A, 117B provide sample addition, subtraction, filtering, or other processing functions as known in the art. Bottom cap 119 provides a means to insert, remove or replace processing elements 117A, 117B in the device. Drip tube 111 provides sample collection from, or discharge into, a sample vessel or container.

Figures 2, 2A:
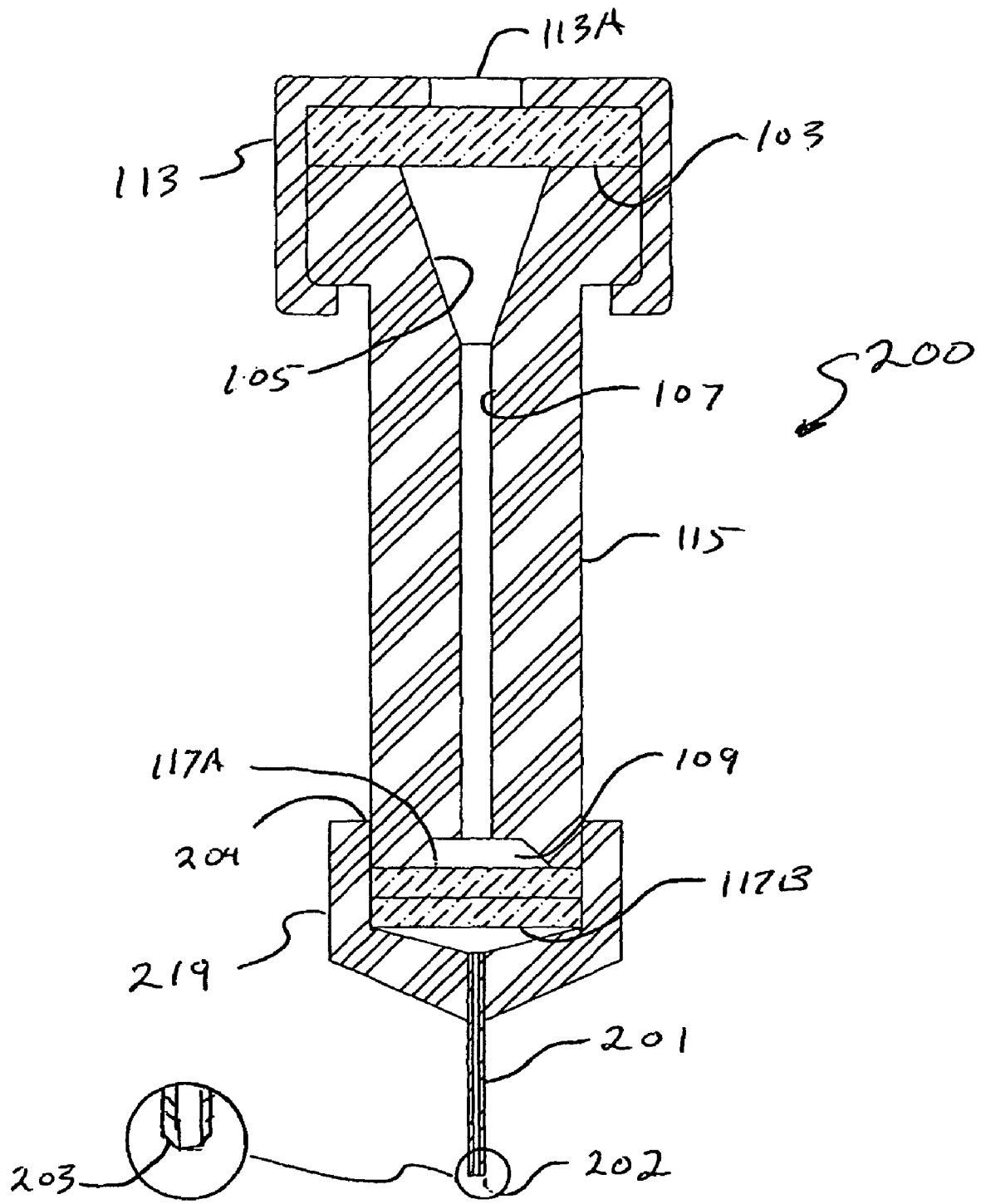
FIG. 2 is cross section elevation drawing of a sample processing/injection device having an injection needle fixed to a removable bottom end cap.
FIG. 2A is a detail cross section drawing of the sealing portion of the injection needle of FIG. 2.

FIG. 2 is a cross section drawing of an improved sample processing/injection device capable of direct sample injection by use of a needle such as injection needle 201 attached to bottom cap 219 of processing/injection device 200. The construction and functions of septum 103, needle guide 105, reduced diameter through chamber 107, sample processing chamber 109, cap 113, body 115 and sample processing elements 117A, 117B is similar to that of FIG. 1. In the preferred embodiments, the device is made of a polymeric material such as polyethylene, polypropylene, or polytetrafluoroethylene.

In the preferred embodiments, injection needle 201 is a metal needle having a length, diameter and end treatment suitable for sample collection from a well, or penetration into a septum such as septum 103 of another vessel or processing device. Needle 201 may have a formed seat surface 202 such as a beveled seat surface 203 of FIG. 2A for seating in other sample receiving apparatus such as sample injection valves of a liquid chromatography instrument as described later. In still other embodiments, needle 201 may be angled for improved septum penetration, or it may have a side opening for other applications.

In the preferred embodiments, needle 201 comprises a blunt end as shown in FIG. 2 and is sized for processing small sample volumes. In one preferred embodiment, needle 201 diameter is selected to form a close fit tolerance with reduced diameter through chamber 107 to allow series connection of the devices. In another embodiment, needle 201 diameter is selected to form a tight or slight interference fit with reduced diameter through chamber 107 to allow positioning of one device by another device.

Needle 201 may be attached to bottom cap 219 of device 200 by press fit, co-molding, or use of mechanical engagement elements such as threads or mechanical joints. In still other embodiments, welding, bonding or adhesives may be used.

In the preferred embodiments, bottom cap 219 is removable from body 115 of the device to allow for insertion, removal or changing of processing elements 117A, 117B, and to allow changing of needle 201. Cap 219 may form an interference, press fit with body 115, forming a liquid seal at seal portion 204. In other embodiments, bottom cap 219 may utilize snap fittings or other mechanical fittings known in the art. In still other embodiments, bottom cap 210 is permanently attached to body 115.

Figure 3:
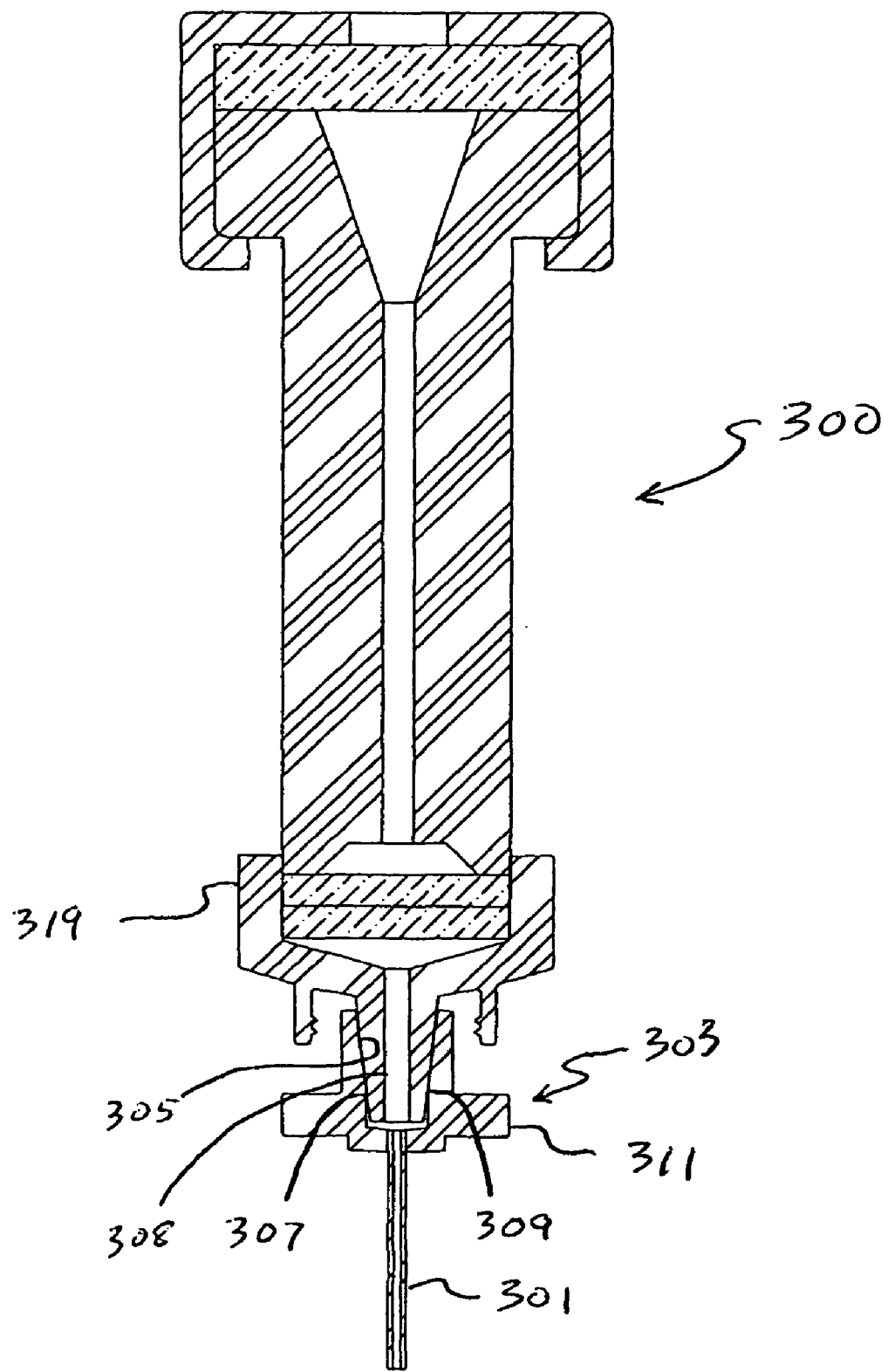
FIG. 3 is cross section elevation drawing of another embodiment of a sample processing/injection device having an injection needle attached to a bottom end cap of the device by a tapered connector such as a luer slip connector.

FIG. 3 is a cross section drawing of another embodiment 300 of the sample processing/injection device of FIG. 2 having a removable needle portion 303 attached to bottom cap 319 of the device. In the preferred embodiments, needle portion 303 comprises a female interference taper fitting or luer slip fitting 305 which form an interference fit with a complementary male luer slip fitting 307. In the preferred embodiments, male luer fitting 307 also functions as a high capacity drip tube on bottom cap 309.

Injection needle 301 is similar to needle 201 of FIG. 2 and is attached to body 311 of needle portion 303 by press fit, snap fit, threaded connection or other means known in the art. In the preferred embodiments, the diameter of bottom cap opening 308 is greater than the opening of injection needle 301 to allow fast sample transfer time with needle 301 removed. Other components of device 300 are similar to those of FIG. 2.

Figure 4:
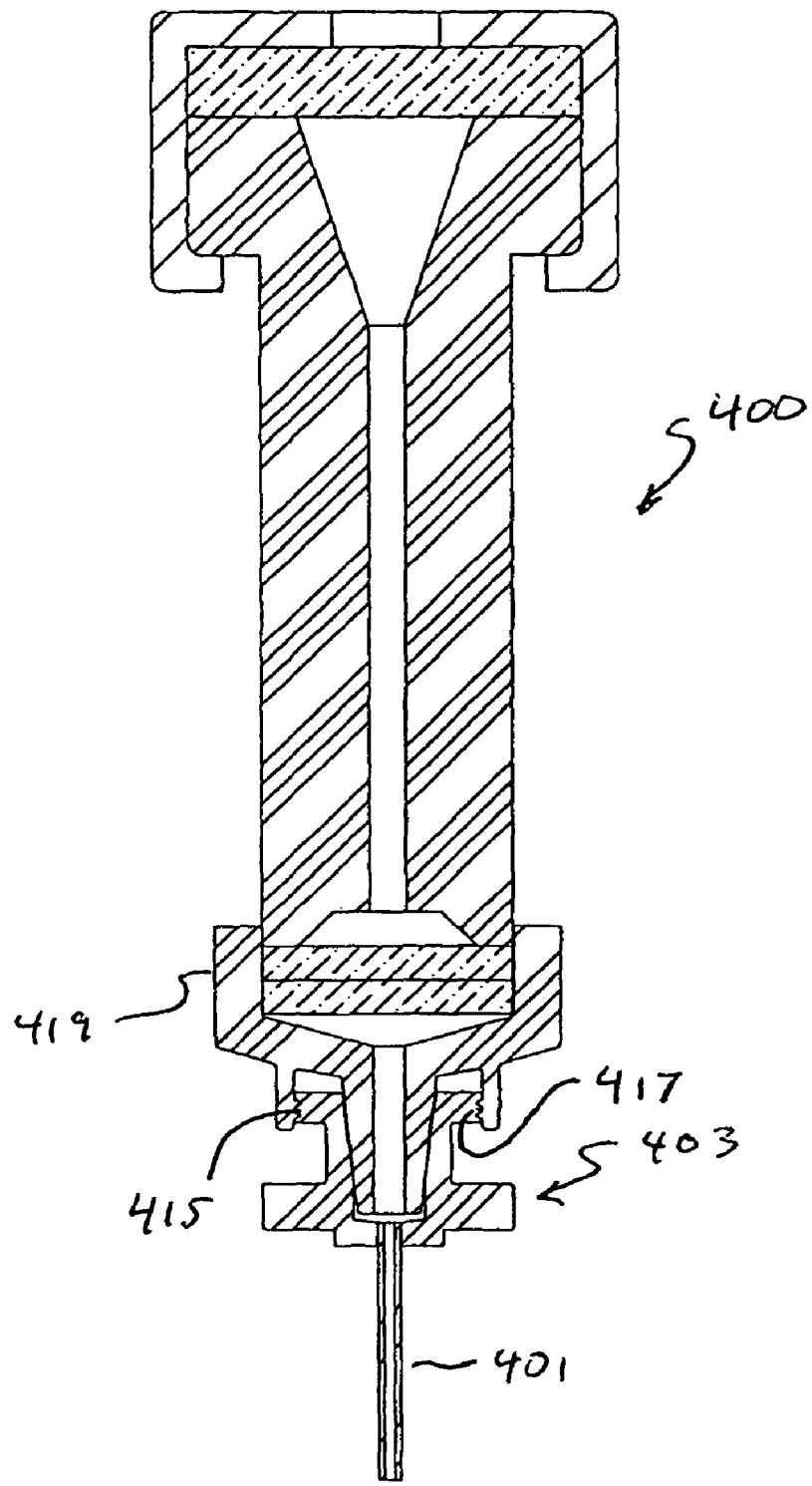
FIG. 4 is cross section elevation drawing of another embodiment of a sample processing/injection device having an injection needle attached to a bottom end cap of the device by a luer lock connector.

FIG. 4 is a cross section drawing of another embodiment 400 of the sample processing/injection device of FIG. 2. Device 400 differs from that of the embodiment of FIG. 3 in that needle portion 403 incorporates locking threads 415 that engage complementary locking threads such as luer lock threads 417 of bottom cap 419 to securely retain needle portion 403 to bottom cap 419. Other components of device 400 are similar to those of the earlier embodiments. In still other embodiments, other connector means such as snap fittings or compression fittings may be used to attach the injection needle to the bottom cap or body of the device.

FIGS. 5A-5L show a preferred embodiment of a method of utilizing the sample processing/injection device to reduce processing steps and improve productivity during sample processing and testing.

FIG. 5A is a schematic diagram of two sample processing/injection devices 300A, 300B disposed in wells of a standard multi-well sample tray 501 and accessed by a needle such as transfer needle 503 of an automated processing instrument 502. In the preferred embodiments, reduced diameter through chamber 107 is selected to form a close fit or slight interference fit with transfer needle 503 and the reduced diameter through chamber comprises a length of at least 5 times the diameter of the chamber to provide alignment of transfer needle 503 and device 300A. A tight or slight interference fit also provides sufficient grip between needle 503 and the device to allow handling and precise movement and positioning of the device with needle 503. In the preferred embodiments, a close tolerance fit is less than 0.005 on the diameter. In the preferred embodiments, a slight interference fit is less than 0.005 on the diameter.

Needle guide 105 provides guidance for needle 503 during insertion of the needle as shown by arrow 505. Needle stop 507 provides control of insertion depth as shown in the needle-inserted position shown in phantom lines.

FIG. 5B is a schematic diagram of device 300A withdrawn vertically in direction 505A from well 501A by the interference fit of needle 503 and chamber 107. In the preferred embodiments, the length of chamber 107 is chosen to be at least 5 and preferably at least 10 diameters of chamber 107 in order to provide axial alignment for precision placing of device 300A.

FIG. 5C is a schematic diagram of device 300A withdrawn from well 501A and being displaced horizontally in direction 505B to another processing location by needle 503 of the automated processing instrument.

FIG. 5D is a schematic diagram of device 300A positioned vertically above needle portion 303A in well 521A of tray 521. Device 300A is positioned vertically downward in the direction of arrow SOS by needle 503 of the automated processing instrument. As needle 503 positions device 300A downward, male luer slip fitting 307 of bottom cap 319 engages to form an interference fit with female luer slip fitting 305 of needle portion 303A as shown in FIG. 5E. Needle stop 507 of needle 503 provides the interference fit insertion force and ledge 522 of well 521 provides a reaction structure to accomplish the secure attachment of needle portion 303A to device 300A.

FIG. 5E is a schematic diagram of device 300A with needle portion 303A attached positioned vertically upwards in the direction of arrow 505A by needle 503 of the processing instrument.

FIG. 5F is a schematic diagram of device 300A with needle portion 303A attached positioned horizontally in the direction of arrow 505B by needle 503 of the processing instrument.

Figure 5I:
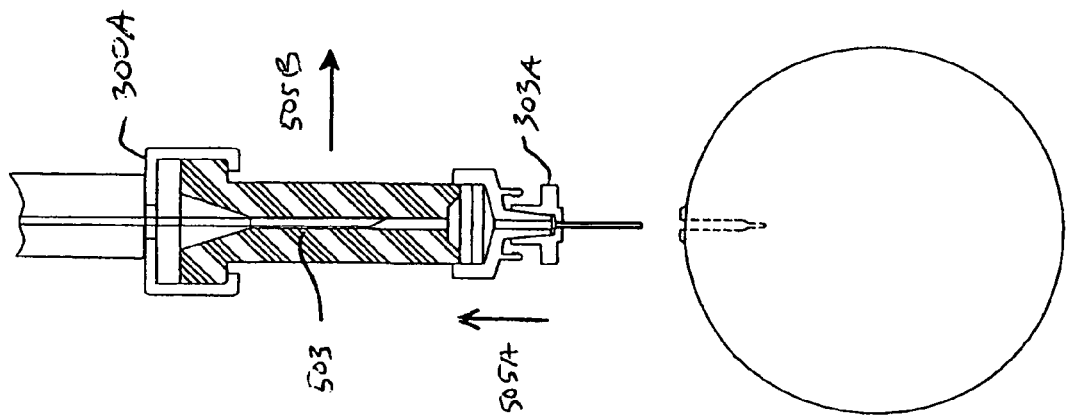
Figure 5H:
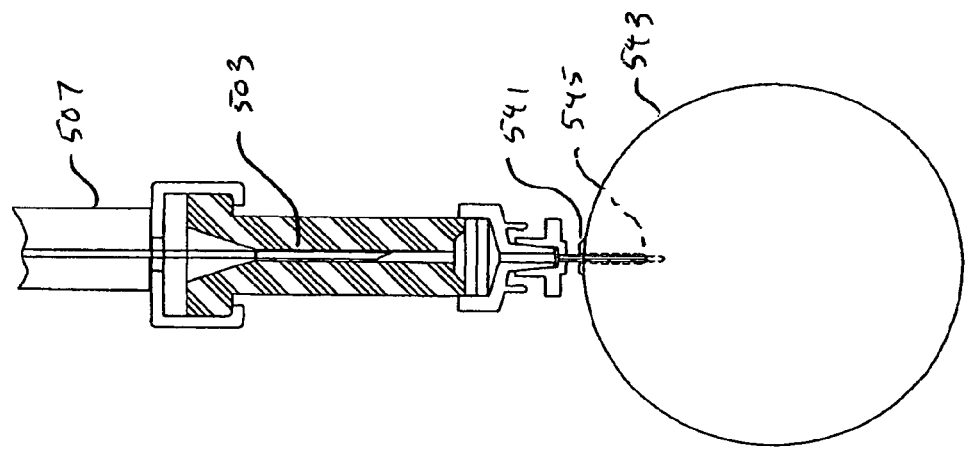
Figure 5G:
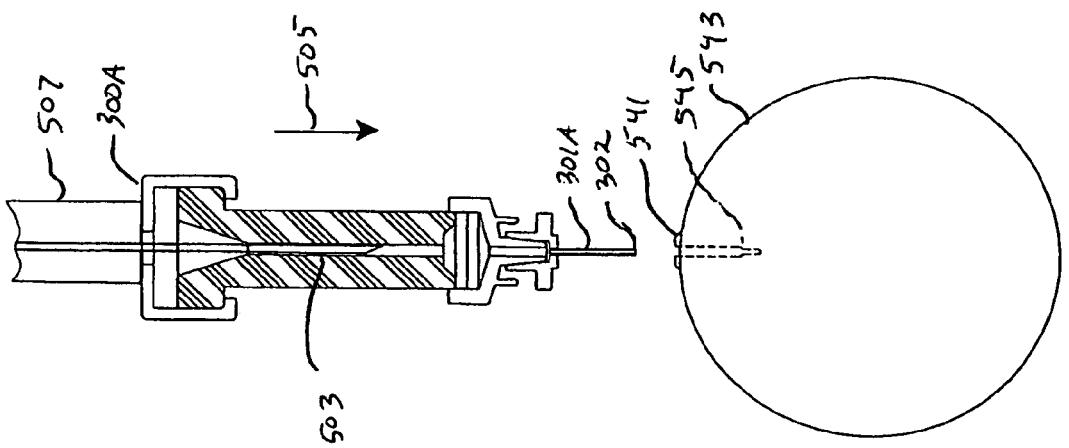

FIG. 5G is a schematic diagram of device 300A positioned vertically above a sample injection port such as injection port 541 of sample injection valve 543 and being positioned vertically downward in the direction of arrow 505 by needle 503 of the automated processing instrument. As needle 503 positions device 300A downward, valve-seating surface 302 of needle 301A engages injection valve seat 545 as shown in FIG. 5H. Needle stop 507 of needle 503 provides the injection valve seating insertion force against seat 545 to accomplish the necessary sealing of device 300A to injection valve 543. The accomplishment of this step allows injection of sample volume directly from sample processing/injection device 300A into injection valve 543 for instrument processing.

FIG. 5I is schematic diagram of device 300A with needle portion 303A attached positioned vertically upwards in the direction of arrow 505A and horizontally in the direction of arrow 505B by needle 503 of the processing instrument.

FIG. 5J is a schematic diagram of device 300A positioned vertically above a sample device receiving component such as multi well tray 561 and being positioned vertically downward in the direction of arrow 505 by needle 503 of the automated processing instrument. As needle 503 positions device 300A downward against device support surface 563 of tray 561 a device retaining element 565 is inserted by the processing instrument as shown in FIG. 5K. Upon withdrawal of needle 503 in the direction of arrow 505A, retaining element 565 retains device 300A in well 561A. The interference fit of needle 503 in reduced diameter through chamber 107 is overcome by the upwards motion of needle 503 and provides automated separation of device 303A and needle 503 as shown in FIG. 5L.

Although the process steps of FIGS. 5A-5L are shown for the embodiment of FIG. 3, similar process steps can be used for other device embodiments. For example, the fixed needle 201 attachment of FIG. 2 would eliminate the necessity of steps 5D and 5E. The embodiment of FIG. 4 would require an additional step of rotation of needle portion 403 in order to secure or unlock needle portion 403 from bottom cap 419. In still other embodiments, the female taper portion of the connectors of embodiments 300 and 400 allow sample intake and elution directly from the device, similar to drip tube 111 of FIG. 1. In still other embodiments, sample is withdrawn or discharged by needle 503 during any of the process sequences shown in FIGS. 5A-5L.

Although the description above contains many specifications, these should not be construed as limiting the scope of the invention but merely providing illustrations of some of the presently preferred embodiments of this invention. Thus the scope of the invention should be determined by the appended claims and their legal equivalents, rather than by the examples given.

We claim:
1. A sample processing/injection device for processing samples comprising:
 a) a septum disposed on a first end portion of the device and in fluid communication with an injection needle disposed on a second end of the device;
 b) a sample processing chamber comprising a sample processing element disposed between the septum and the injection needle;
 c) a reduced diameter through chamber disposed between the septum and the sample processing chamber, the reduced diameter through chamber comprising a length at least 5 times a diameter of the trough chamber; and, d) a bottom cap provided on a second end portion of the device, the bottom cap having a side wall surrounding the end of the device and a bottom wall extending radially from the side wall and terminating at a central passageway extending therethrough wherein the injection needle extends through the central passageway to fixedly secure the needle to the bottom cap.

2. The device of claim 1 wherein the injection needle comprises a formed seating surface on a tip of the injection needle for seating on a seat of a processing instrument injection valve.

3. The device of claim 1 wherein the injection needle comprises a beveled seating surface on a tip of the injection needle.

4. The device of claim 1 comprising a conical needle guide disposed between the septum and the reduced diameter through chamber.

5. The device of claim 1 wherein the reduced diameter through chamber has a diameter less than the processing chamber.

6. The device of claim 5 wherein the injection needle comprises a diameter forming a close fit tolerance with the reduced diameter through chamber.

7. The device of claim 5 wherein the injection needle comprises a diameter forming a slight interference fit with the reduced diameter through chamber.

8. The device of claim 1 and wherein the bottom cap is removable from the device.

9. The device of claim 8 wherein the bottom cap is attached to a body portion of the device by an interference fit.

10. The device of claim 1 and wherein the bottom cap is permanently fixed to the device.

11. The device of claim 1 and wherein the injection needle is secured to the cap by at least one of adhesive bonding, welding, co-molding, press fitting, threads or a mechanical joint.

* * * * *